United States Patent [19]
Dai et al.

[11] Patent Number: 5,822,072
[45] Date of Patent: Oct. 13, 1998

[54] FIBEROPTIC PROBE AND SYSTEM FOR SPECTRAL MEASUREMENTS

[75] Inventors: Sheng Dai, Knoxville; Jack P. Young, Oak Ridge, both of Tenn.

[73] Assignee: Lockheed Martin Energy Systems, Inc., Oak Ridge, Tenn.

[21] Appl. No.: 792,510

[22] Filed: Jan. 31, 1997

Related U.S. Application Data

[63] Continuation of Ser. No. 316,306, Sep. 30, 1994, abandoned.

[51] Int. Cl.⁶ .................................................. G01N 21/00
[52] U.S. Cl. ...................... 356/436; 385/12; 250/227.23
[58] Field of Search .............................. 356/73, 336, 133, 356/128, 432, 436, 440, 301, 317, 318, 416, 446, 326; 250/458.1, 459.1, 461.1, 461.2, 227.11, 227.23, 227.24, 227.28; 385/12, 31, 38, 85, 88, 115, 116, 133

[56] References Cited

U.S. PATENT DOCUMENTS

| | | | |
|---|---|---|---|
| 4,573,761 | 3/1986 | McLachlan et al. | 356/301 X |
| 5,013,150 | 5/1991 | Watts et al. | 356/73 |
| 5,112,127 | 5/1992 | Carrabba et al. | 356/301 |
| 5,155,549 | 10/1992 | Ohadwal | 356/336 |
| 5,201,022 | 4/1993 | Shifflet | 385/128 |
| 5,293,438 | 3/1994 | Konno et al. | 385/35 |
| 5,381,237 | 1/1995 | Sela | 356/133 |
| 5,402,508 | 3/1995 | O'Rourke et al. | 385/31 |

FOREIGN PATENT DOCUMENTS 62-91840  4/1987  Japan ..................................... 356/326

OTHER PUBLICATIONS

F. B. Shand, Chapter 9, "Glass Engineering Handbook," Second Ed., 1958, pp. 176–184.

Ovadia Lev, et al, "A High–Sensitivity Photometric Method Based on Doped Sol–Gel Glass Detectors: Determination of Sub–ppb Divalent Iron," *Fresenius J. Anal. Chem.*, 343 (1992), pp. 370–372.

Chongmok Lee et al, "Scanning Electrochemical Microscopy:Preparation of Submicrometer Electrons," *Analytical Chem.*, 63 (1991), pp. 78–83.

Sheng Dai et al., "Measurement of Molten Salt Raman Spectra by the Use of Fiber Optics," *Mikrochim. Acta*, 108 (1992), pp. 261–264.

A. Kumar, et al, "Novel Refractometer Using a Tapered Optical Fibre," *Electronics Letters*, 20 (1984), pp. 534–535.

Primary Examiner—K. Hantis
Attorney, Agent, or Firm—Shelley L. Stafford

[57] ABSTRACT

A fused fiberoptic probe, a system, method and embodiments thereof for conducting spectral measurements are disclosed. The fused fiberoptic probe comprises a probe tip having a specific geometrical configuration, an exciting optical fiber and at least one collection optical fiber fused within a housing, preferably silica. The specific geometrical configurations in which the probe tip can be shaped include a slanted probe tip with an angle greater than 0°, an inverted cone-shaped probe tip, and a lens head.

12 Claims, 9 Drawing Sheets

FIBEROPTIC PROBE AND SYSTEM FOR SPECTRAL MEASUREMENTS

CROSS REFERENCES TO RELATED APPLICATIONS

This application is a continuation of application Ser. No. 08/316,306, filed Sep. 30, 1994, now abandoned.

This invention was made with Government support under contract DE-AC05-84OR21400 awarded by the Office of Industrial Processes, U.S. Department of Energy to Martin Marietta Energy Systems, Inc., and the Government has certain rights in this invention.

FIELD OF THE INVENTION

The present invention relates to instrumentation for measuring light scattering and luminescence, particularly to a fused fiberoptic probe exhibiting improved performance for conducting spectral measurements, more particularly for conducting Raman spectral measurements in samples remote from the optical energy-generating source and signal analyzer.

BACKGROUND OF THE INVENTION

Measuring certain physical and chemical characteristics using light has been known in laboratories for many years. Spectroscopic techniques are frequently used in laboratories for both qualitative and quantitative analyses. The combination of lasers and optical fibers have greatly increased activity in this field. The use of optical fibers, in particular, have allowed the locating of sensitive and expensive equipment remote from harsh reactor environments, thus making spectroscopic analysis techniques suitable for application to commercial processes.

Vibrational spectroscopy is a useful technique for characterizing molecules and for determining their chemical structure. The vibrational spectrum of a molecule, based on the molecular structure of that molecule, is a series of sharp lines which constitutes a unique fingerprint of that specific molecular structure. For process control or for analyses of samples in remote or hostile environments, it is often desirable to measure the vibrational spectrum of a sample in that process stream or environment. If the vibrational spectrum is to be measured by an optical absorption process, optical fibers must be used so that optical energy from a source is delivered to a sample via one fiber, and after passage through the sample, an optical signal generated by the exciting optical energy is collected by the same or, more preferably, another fiber. This collected light is directed to a monochrometer/or a photodetector for analyzing its wavelength and/or intensity.

One analytical technique that is useful for commercial applications is Raman spectroscopy. When exciting optical energy of a single wavelength interacts with a molecule, the optical energy scattered by the molecule contains small amounts of optical energy having wavelengths different from that of the incident exciting optical energy. This is known as the Raman effect. The wavelengths present in the scattered optical energy are characteristic of the structure of the molecule, and the intensity of this optical energy is dependent on the concentration of these molecules. Thus, the identities and concentrations of various molecules in a substance can be determined by illuminating the substance with energy of a single wavelength and then measuring the individual wavelengths, and their intensities, in the scattered optical energy.

Raman spectroscopy provides a means for obtaining similar molecular vibrational spectra over optical fibers using visible or near infrared light that is transmitted by the optical fibers without significant absorption losses. In Raman spectroscopy, monochromatic light is directed to a sample and the spectrum of the light scattered from the sample is determined. In a typical Raman experiment, the excitation light source is a laser line, such as the 514.5 nm (19435 cm.$^{-1}$) line from an Argon ion gas laser. The Raman effect is not usually a sensitive effect; most of the light scattered from the sample will also be of the exciting wavelength (the Rayleigh line). Approximately 1 part in $10^6$ will be scattered at wavelengths containing the sum or difference of the Rayleigh and allowed molecular vibrational frequencies. For example, if a molecule has a Raman active vibration at 5 $\mu$m (2000 cm$^{-1}$), the line will appear in the scattered light spectrum at 19435+2000 cm$^{-1}$ or 466 nm. Since this scattered signal is very weak, an intense exciting source, such as a laser, is preferable and the optical arrangement for receiving these signals should be optimized.

Measurements of laser Raman spectroscopy using optical fibers have recently become an active area of study. The technique requires minimum alignment of samples with respect to an input laser beam or collection optics, and the sample may be located some distance from the spectrometer in a hostile environment. So far, most of the probes employed in these measurements have been constructed by sealing the collection optical fibers and one laser input fiber into a metal or glass protective tube with an epoxy cement. This imposes difficulties for the measurement of Raman spectra with these probes in some hostile environments due to chemical and/or thermal reactions of the epoxy resin with surrounding molecules. The measurement of molten salt Raman spectra is an example in which the extremely corrosive conditions and high temperatures involved are enough to degrade the epoxy materials.

Obtaining Raman spectra through optical fibers over long distances is historically difficult. Sending intense laser light through long lengths of optical fiber gives rise to false optical signals that originate both from fluorescence and Raman scattering arising from the fiber core and cladding. Similarly, the scattered Rayleigh radiation can interfere with the spectral signals that lie close to the Rayleigh frequency. Both of these problems can require optical components for filtering the exciting and scattered light. In U.S. Pat. No. 5,112,127 by Carrabba and Rauh, these filters are placed at the sampling end of the optical fiber bundle. As placed, the filters are extra components that are subject to chemical and thermal attack by the sample.

U.S. Pat. No. 4,573,761 by McLachlan et al describes apparatus and optical fiber configurations in which the collection fibers are cemented at an angle with respect to the excitation fiber to improve signal collection efficiency for remote Raman spectroscopy. This patent also describes the utilization of diamond windows for the determination of species which exhibit Raman spectra in remote corrosive environments. Diamond windows, although useful in minimizing corrosion, are highly reflective and therefore degrade the intensity of signals coming from outside of the diamond. This patent, however, does not address the problem of removing the. spurious or false optical signals originating in the excitation and collection fibers.

Sheng Dai et al describe in *Mikrochimica Acta* (1992), volume 108, the fabrication of a fused all-silica fiberoptic probe having a flat probe tip and its use for obtaining Raman spectra of various molten salt systems at temperatures up to 720° C. The fiberoptic probe has also been used for Raman spectral studies of samples at ambient temperatures.

A need exists for continuous or semi-continuous analytical sensors to determine the concentration of soluble magnesium ion in the chloride molten salts used in the electrolytic production of magnesium metal. Magnesium is generally produced by the electrolysis of molten magnesuim chloride derived from either hydrated salt (Dow Chemical Company) or anhydrous salt obtained from dolomite or other sources. The electrolyte bath is usually composed of $NaCl-KCl-CaCl_2-MgCl_2$,(35-35-15-15 mole %), and generally contains impurities such as hydroxides, oxides, sulphates and metallic ions as well as additives such as fluorides. In-line analytical sensors would better control the electrolytic reduction of magnesuim. It is estimated that up to 5% of the energy costs related to magnesium production can be saved if the soluble magnesium ion concentration in the melt is continuously monitored.

Despite the advances disclosed in the prior art, a need does exist for a fiberoptic probe with improved performance for conducting spectral measurements that is able to withstand very low or high temperatures or corrosive, hostile environments, particularly in samples remote from the generating optical energy source and signal analyzer. Therefore, a fiberoptic probe is needed which yields improved performance and requires no epoxy resin or cement to fix the probe tip geometry. Applicants' probe offers a solution to the need for improved performance and durability. Applicants' probe is a fiberoptic probe wherein the optical fibers are sealed in fused silica, essentially forming a fused silica rod, with a probe tip that is shaped into unique specific geometrical configurations that are dependent upon the index of refraction of the sample to be analyzed. Applicants' probe is fabricated with specific geometrical probe tip configurations for greater optical coupling efficiency of the exciting and collection optical fibers at the sample interface. The unique specific geometrical configurations in which the probe tip can be shaped include a slanted probe tip with an angle greater than 0°, a probe-tip having a conical indentation at its tip, co-axial with the longitudinal axis, hereinafter referred to as an inverted cone-shaped probe tip, and a lens head. Applicants' probe requires no epoxy resin or cement to fix the probe tip geometry. Since the optical fibers are sealed in fused silica at the probe tip of the fiberoptic probe, there is no failure of the probe at very low or high temperatures or in hostile environments. The angle of the probe tip is generated by grinding and polishing the optical fiber probe tip and can be shaped by standard optical machining practice. Since applicants' probe is constructed as a fused silica fiberoptic probe, no protective window, which introduces reflectance problems, is necessary. Applicants' design is useful for any spectroscopy that uses scattered light, such as Raman, fluorescence, scattered reflection, etc., in a much wider variety of sampling situations. Optical filtering can be carried out away from the sample interface.

OBJECT OF THE INVENTION

It is an object of the invention to provide new instrumentation for environmental monitoring, characterizing, and locating of hazardous wastes in a timely, cost-effective manner.

It is another object of the invention to provide new methods of environmental monitoring, characterizing, and locating of hazardous wastes in a timely, cost-effective manner.

It is still a further object of the invention to provide new instrumentation for measuring both light scattering and luminescence.

It is another object of the invention to provide new instrumentation particularly for conducting Raman spectral measurements.

It is yet another object of the invention to provide a new method for measuring light scattering and luminescence.

It is still a further object of the invention to provide a new method for conducting Raman spectral measurements.

It is another object of the invention to provide new instrumentation for measuring both light scattering and luminescence in samples in remote and hostile environments.

It is yet another object of the invention to provide new instrumentation for conducting Raman spectral measurements in samples in remote and hostile environments.

It is still a further object of the invention to provide continuous or semi-continuous analytical sensors to determine the concentration of soluble magnesium ion in chloride molten salts used in the electrolytic production of magnesium metal.

Further and other objects of the present invention will become apparent from the description contained herein.

SUMMARY

In accordance with one aspect of the present invention, the foregoing and other objects are achieved by a fused fiberoptic probe for conducting spectral measurements which comprises an immersible probe head having a slanted probe tip with an angle greater than 0°, an exciting optical fiber and at least one collection optical fiber. The exciting optical fiber has a terminus at the probe tip for transmitting exciting optical energy to the probe tip in order to generate an optical signal within the sample medium. The collection optical fiber has a terminus at the probe tip. The collection optical fiber is fused with the exciting optical fiber at the probe head, thereby forming the probe head. The terminuses of the exciting optical fiber and the collection optical fiber form the probe tip. The collection optical fiber is for transmitting the optical signal from the probe tip.

In accordance with another aspect of the present invention, other objects are achieved by a fused fiberoptic probe for conducting spectral measurements which comprises an exciting optical fiber having a terminus and at least two collection optical fibers, each having a terminus. The fiberoptic probe further comprises an immersible probe head having a longitudinal axis and a perpendicular axis which forms an angle with the terminuses of the exciting optical fiber and the collection optical fibers. The perpendicular axis intersects the longitudinal axis. The probe head further having an inverted cone-shaped probe tip wherein the terminuses of the exciting optical fiber and the collection optical fibers are within the concial surface of the inverted cone of the conical indentation and thus are angled toward the longitudinal axis at an angle between 10° and 85° with respect to the perpendicular axis, the angle being dependent upon the effective index of refraction of a sample medium. The inverted cone-shaped probe tip has a center apex, the center apex being intersected by the longitudinal axis. The exciting optical fiber's terminus is at the center apex of the inverted cone-shaped probe tip for transmitting exciting optical energy to the probe tip in order to generate an optical signal within the sample medium. The collection optical fibers are juxtaposed with the exciting optical fiber. The collection optical fibers are fused with the exciting optical fiber at the probe head, thereby forming the probe head. The terminus of the exciting optical fiber and the terminuses of the collection optical fibers are within the conical surface of the concial indentation of the inverted cone-shaped probe tip. The collection optical fibers are for transmitting the optical signal from the probe tip.

In accordance with yet another aspect of the present invention, other objects are achieved by a fused fiberoptic probe for conducting spectral measurements which comprises a housing, an immersible probe head, wherein the probe head has a probe tip and a lens disposed on the probe tip. The fiberoptic probe further comprises an exciting optical fiber and at least one collection optical fiber. The exciting optical fiber is disposed within the housing and the exciting optical fiber has a terminus at the probe tip for transmitting exciting optical energy to the probe tip in order to generate an optical signal within a sample medium. The collection optical fiber is disposed within the housing and the collection optical fiber has a terminus at the probe tip. The collection optical fiber is fused with the exciting optical fiber at the probe head, thereby forming the probe head and the terminus of the exciting optical fiber and the terminus of the collection optical fiber form the probe tip. The collection optical fiber is for transmitting the optical signal from the probe tip.

In accordance with another aspect of the present invention, a new method for conducting spectral measurements comprises the steps of:

Step 1. Providing a fused fiberoptic probe which comprises an immersible probe head having a slanted probe tip with an angle greater than 0°. The fiberoptic probe further comprises an exciting optical fiber and at least one collection optical fiber. The exciting optical fiber has a terminus at the probe tip for transmitting exciting optical energy to the probe tip in order to generate an optical signal within a sample medium. The collection optical fiber has a terminus at the probe tip. The collection optical fiber is fused with the exciting optical fiber at the probe head, thereby forming the probe head, and the terminus of the exciting optical fiber and the terminus of the collection optical fiber forms the probe tip. The collection optical fiber is for transmitting the optical signal from the probe tip.

Step 2. Immersing the probe head of the fiberoptic probe into the sample medium.

Step 3. Transmitting exciting optical energy into the exciting optical fiber of the fiberoptic probe wherein the exciting optical energy is transmitted to the probe tip for generating an optical signal within the sample medium.

Step 4. Transmitting the optical signal from the probe tip through the collection optical fiber to a signal analyzer.

In accordance with still another aspect of the present invention, a new method for conducting spectral measurements comprises the steps of:

Step 1. Providing a fused fiberoptic probe for conducting spectral measurements which comprises an exciting optical fiber having a terminus and at least two collection optical fibers, each having a terminus. The fused fiberoptic probe further comprises an immersible probe head having a longitudinal axis and a perpendicular axis which forms an angle with the terminuses of the exciting optical fiber and the collection optical fibers. The perpendicular axis intersects the longitudinal axis. The probe head further having an inverted cone-shaped probe tip wherein the terminuses of the exciting optical fiber and the collection optical fibers are angled toward the longitudinal axis at an angle between 10° and 85° with respect to the perpendicular axis, the angle being dependent upon the effective refractive index of a sample medium. The inverted cone-shaped probe tip has a center apex, the center apex being intersected by the longitudinal axis. The exciting optical fiber has the terminus at the center apex of the inverted cone-shaped probe tip. The exciting optical fiber is for transmitting exciting optical energy to the probe tip in order to generate an optical signal with the sample medium. The collection optical fibers are juxtaposed with the exciting optical fiber. The collection optical fibers are fused with the exciting optical fiber at the probe head, thereby forming the probe head, and the terminus of the exciting optical fiber and the terminuses of the collection optical fibers are within the concial surface of the conical indentation of the inverted cone-shaped probe tip. The collection optical fibers are for transmitting the optical signal from the probe tip.

b) Immersing the probe head into the sample medium.

c) Transmitting exciting optical energy into the exciting optical fiber wherein the exciting optical energy is transmitted to the probe tip for generating an optical signal within the sample medium.

d) Transmitting the optical signal from the probe tip through the collection optical fibers to a signal analyzer.

In accordance with yet another aspect of the present invention, a new method for conducting spectral measurements comprises the steps of:

a) Providing a fused fiberoptic probe which comprises an exciting optical fiber having a terminus and at least two collection optical fibers, each having a terminus. The fused fiberoptic probe further comprises a probe head having a longitudinal axis and a perpendicular axis which forms an angle with the terminuses of the exciting optical fiber and the collection optical fibers. The perpendicular axis intersects the longitudinal axis. The probe head further having an inverted cone-shaped probe tip wherein the terminuses of the exciting optical fiber and the collection optical fibers are angled toward the longitudinal axis at an angle between 10° and 85° with respect to the perpendicular axis, the angle being dependent upon the effective refractive index of a sample medium. The inverted cone-shaped probe tip has a center apex, the center apex being intersected by the longitudinal axis. The exciting optical fiber has the terminus at the center apex of the inverted cone-shaped probe tip. The exciting optical fiber is for transmitting exciting optical energy to the probe tip in order to generate an optical signal within the sample medium. The collection optical fibers are juxtaposed with the exciting optical fiber. The collection optical fibers are fused with the exciting optical fiber at the probe head, thereby forming the probe head, and the terminus of the exciting optical fiber and the terminuses of the collection optical fibers are within the concial surface of the conical indentation of the inverted cone-shaped probe tip. The collection optical fibers are for transmitting the optical signal from the probe tip.

b) Inverting the fiberoptic probe wherein the inverted cone-shaped probe tip serves as a spectroscopic container.

c) Placing a sample within the cone.

d) Transmitting exciting optical energy into the exciting optical fiber wherein the exciting optical energy is transmitted to the probe tip for generating an optical signal within the sample medium.

e) Transmitting the optical signal from the probe tip through the collection optical fibers to a signal analyzer.

In accordance with another aspect of the present invention, a method for conducting spectral measurements comprises the steps of:

a) Providing a fused fiberoptic probe which comprises a housing, an immersible probe head having a probe tip and a lens disposed on the probe tip. The fused fiberoptic probe further comprises an exciting optical fiber and at least one collection optical fiber. The exciting optical fiber is disposed within the housing and the exciting optical fiber having a terminus at the probe tip. The exciting optical fiber is for transmitting exciting optical energy to the probe tip in order to generate an optical signal within a sample medium. The collection optical fiber is disposed within the housing and the collection optical fiber having a terminus at the probe tip. The collection optical fiber is fused with the exciting optical fiber at the probe head, thereby forming the probe head and the terminus of the exciting optical fiber and the terminus of the collection optical fiber are within the conical surface of the inverted cone of the conical indentation and thus form the probe tip. The collection optical fiber is for transmitting the optical signal from the probe tip.

b) Immersing the probe head into the sample medium.

c) Transmitting exciting optical energy into the exciting optical fiber wherein the exciting optical energy is transmitted to the probe tip for generating an optical signal within the sample medium.

d) Transmitting the optical signal from the probe tip through the collection optical fiber to a signal analyzer.

BRIEF DESCRIPTION OF THE DRAWINGS

For a better understanding of the present invention, together with other and further objects, advantages and capabilities thereof, reference is made to the following disclosure and appended claims when read in connection with the appended drawings, wherein:

DETAILED DESCRIPTION OF THE INVENTION

The subject invention is a novel yet practical approach for conducting spectral measurements, both light scattering and luminescence, in samples remote from the generating optical energy source and signal analyzer. Applicants' fiberoptic probe generally comprises a probe head, an exciting optical fiber and at least one collection optical fiber fused at the probe head within a housing, preferably an all-silica housing, essentially forming a fused silica rod. The probe head has a probe tip shaped into unique specific geometrical configurations that are dependent upon the effective index of refraction of the sample to be analyzed. Applicants' probe is fabricated with specific geometrical probe tip configurations for greater optical coupling efficiency of the exciting and collection optical fibers at the sample interface. The unique specific geometrical configurations in which the probe tip can be shaped include a slanted probe tip with an angle greater than 0°, an inverted cone-shaped probe tip, and a probe tip with a lens disposed on the tip. The optical fibers are silica as well.

Figure 1:
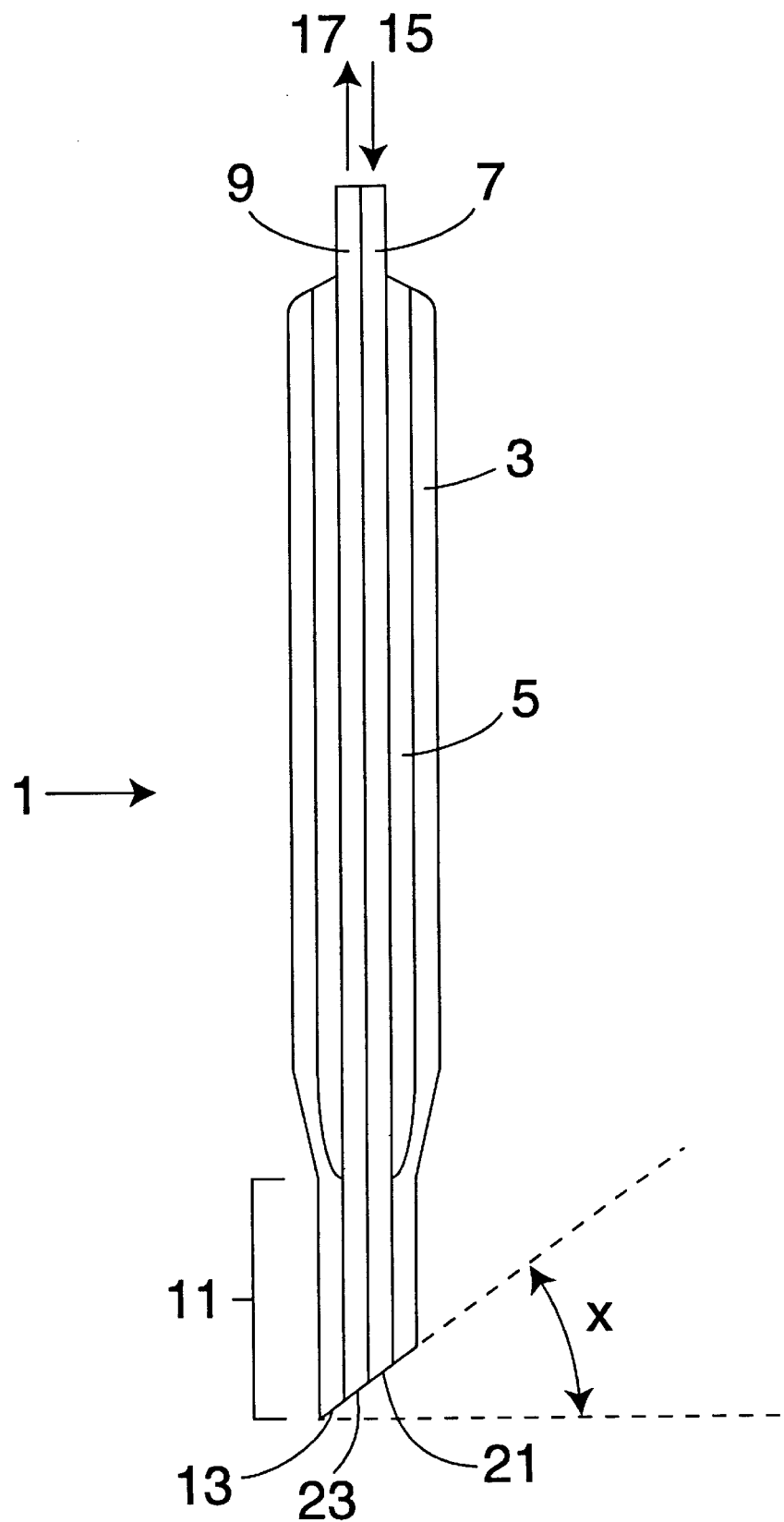
FIG. 1 shows a sectional view of a fused fiberoptic probe with the probe head having a slanted probe tip in accordance with one embodiment of the invention.

FIG. 1 shows one embodiment of Applicants' invention, a slanted-tip fiberoptic probe 1. This design of the fiberoptic probe aids in collecting scattered light and luminescence 17, such as Raman signals, generated by optical energy, such as laser light 15, from an optical energy source. Experimentally, it was found that the slanted-tip probe minimizes the collection of the quartz Raman signals generated in the exciting optical fiber 7. Referring to FIG. 1, the fiberoptic probe 1 comprises two parallel optical fibers 7, 9, an exciting optical fiber 7 and a collection optical fiber 9, that are fused within an all-silica housing 3 at the probe head 11. The optical fibers terminate at their respective terminuses 21, 23 in a probe tip 13 having a slanted tip with an angle x greater than 0°. The probe tip 13 and probe head 11 is immersible in a sample. The probe head 11 is the region of the fiberoptic probe where the housing 3 and the optical fibers 7 and 9 are fused together, actually forming or defining the probe head and then their terminuses are shaped into the slanted tip 13. Because the fusion of the optical fibers 7, 9 with the housing 3, only at the probe head 11, air pockets 5 are created between the housing 3 and the optical fibers 7, 9. The exciting optical fiber 7 transmits optical energy 15 from any suitable optical energy source (FIG. 12), such as a laser (18 of FIG. 12), to its terminus 21 at the slanted probe tip 13. The optical energy source providing the optical energy is in optical communication with the fiberoptic probe by directing its energy onto the exciting optical fiber 7. The optical energy 15 is transmitted from the slanted probe tip 13 at the terminus of the exciting optical fiber 21 into a sample medium, generating an optical signal 17 from the sample. The optical signal 17 is collected by the collection optical fiber 9 at the slanted probe tip 13 by the terminus 23 of the collection optical fiber and is transmitted from the slanted tip 13, up the collection optical fiber 9 to a signal analyzer (19 of FIG. 12), such as a spectrometer. The signal analyzer (19 of FIG. 12) is in optical communication with the fiberoptic probe. The signal analyzer (19 of FIG. 12) receives the information from the optical signal 17 via the collection optical fiber 9, analyzes and processes that information.

Figure 2:
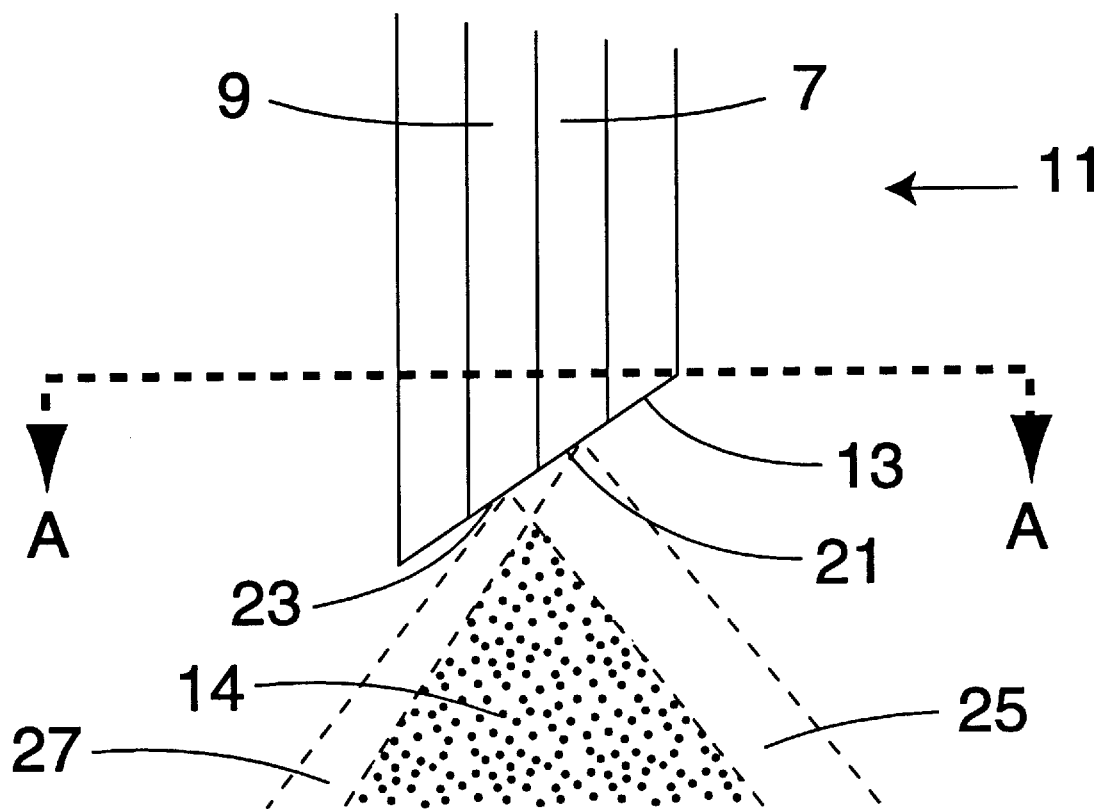
FIG. 2 shows the probe head with the slanted probe tip shown in FIG. 1, illustrating the overlap of the geometry of the viewing cones of the exciting optical fiber and the collection optical fiber.
Figure 3:
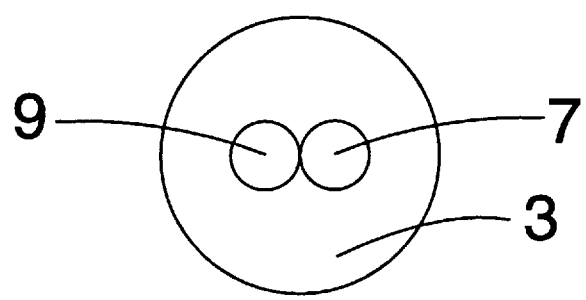
FIG. 3 shows the cross-section from FIG. 2, illustrating the closeness of the exciting optical fiber and collection optical fiber to one another.

This particular embodiment 1 of Applicants' fiberoptic probe can be easily created by cutting and polishing a slanted tip, as shown in FIG. 1, out of the uncut, fused probe tip. When the exciting energy is passed through the upper optical fiber (the exciting optical fiber) 7 and scattered light is collected in the bottom optical fiber (the collection optical fiber) 9, significant improvement of collection efficiency is achieved as compared to the fiberoptic probe with a flat tip, as utilized by Dai et al. Experimentally, it was found that when optical fiber 9 was used as the excitation fiber, the Raman signals observed via optical fiber 7 were very weak. The use of optical fiber 7 as the excitation fiber, however, produced a very intense Raman signal at optical fiber 9. Even the weak Raman band of water at 1650 cm$^{-1}$ was detected with this device. The difference in response is due to the overlap of the geometry 14 of the viewing cones 27 and 25 of optical fibers 7 and 9, respectively, as illustrated in FIG. 2, and to the closeness of the collection optical fiber 9 with the exciting optical fiber 7. FIG. 2 also shows a cross-section cut A that is illustrated in FIG. 3. FIG. 3 illustrates this close relationship of the exciting optical fiber 7 with the collection optical fiber 9, both optical fibers being fused within the housing 3 at the probe head. The closer the optical fibers are to one another, the larger the area of the overlap 14 of FIG. 2. By increasing the area of the overlap 14, the collectible Raman scattering is intensified, thereby increasing the optical signal. This closeness is achievable because the optical fibers 7 and 9 are positioned together by the fusion step in the fabrication of the probe head 11. The arrangement of the present invention in FIG. 1 and FIG. 2 minimizes the background quartz signals. It appears that the collection optical fiber 9 does not pick up the scattered Raman signal from the exciting optical fiber 7, so the quartz interference is minimized. By exciting with the upper optical fiber 7 and collecting with the lower optical fiber 9, better geometrical interaction of the exciting energy and scattered energy is achieved, thus increasing the collection efficiency of the fiberoptic probe.

EXAMPLE I

The described embodiment of the invention of FIG. 1 was fabricated to measure the intensity of the Raman spectrum of the tetrachloromagnesium (II) ion and thereby monitor the concentration of magnesium chloride dissolved in molten chloride salts at 700° C. The performance of the probe was characterized by the measurements of Raman spectra of tetrachloromagnesium (II), tetrachloroaluminum (III) ions, carbon tetrachloride, and absorption and fluorescence spectral measurements of solid EuOCl and adsorbed TbCl$_3$. The measurements were made at temperatures varying from 77 K to 1200 K. The limit of useful temperature for this fiberoptic probe device is the temperature range of solid silica, 0 to ~1800 K. Such spectra were obtained in a corrosive, high-temperature environment. The fiberoptic probe 1 has also been used in many other spectral areas, such as Raman spectral studies of liquids from 77 to 1200 K, fluorescence spectral studies of solid TbCl$_3$ from 77 to 300 K, reflectance spectral studies of solid EuOCl$_3$ from 77 to 1300 K, as well as solution absorption spectral studies.

EXAMPLE II

Figure 4:
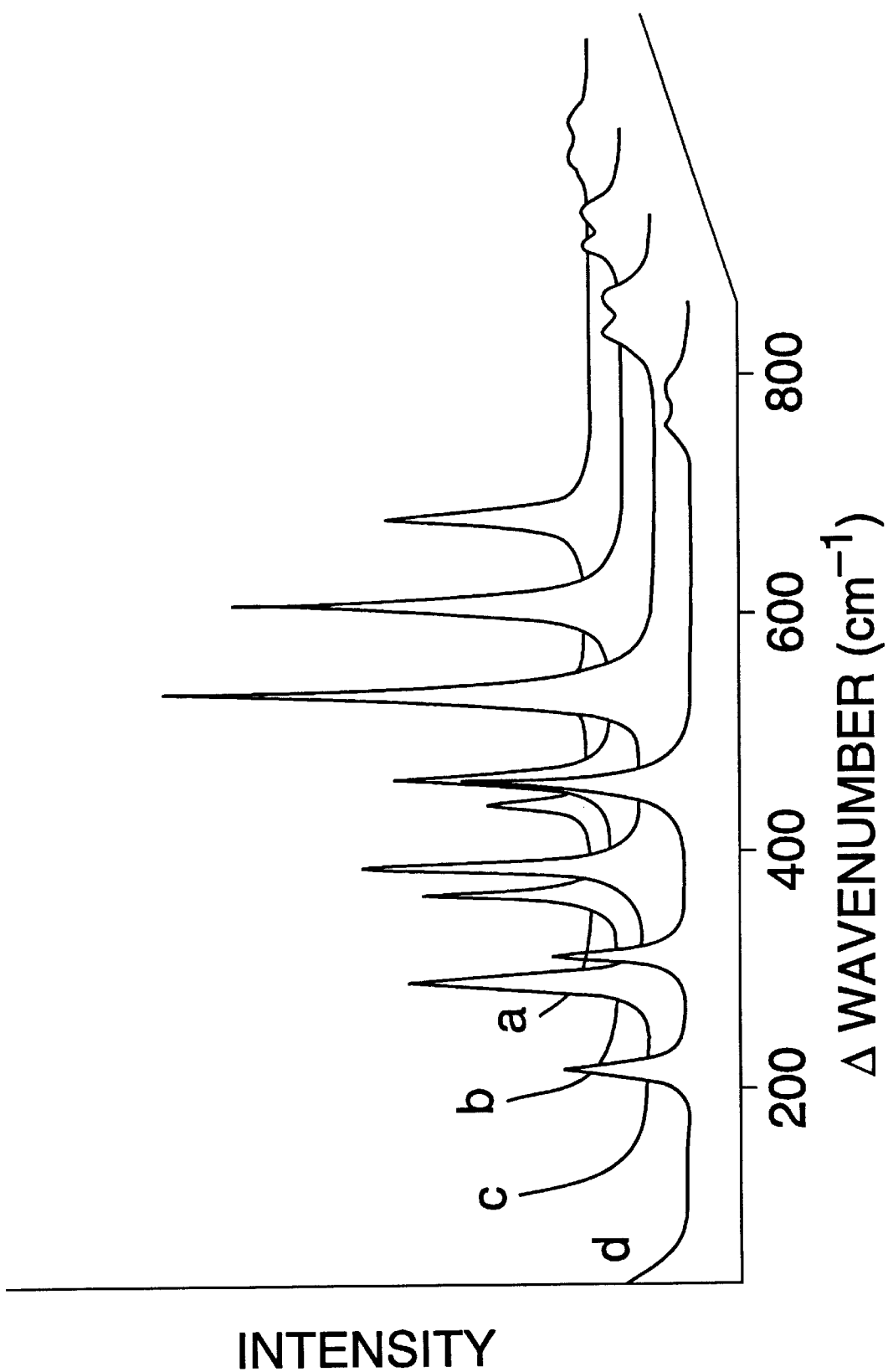
FIG. 4 shows the Raman spectra of carbon tetrachloride, measured in accordance with the invention, with varying angles of the slanted fiberoptic probe tip.
Figure 5:
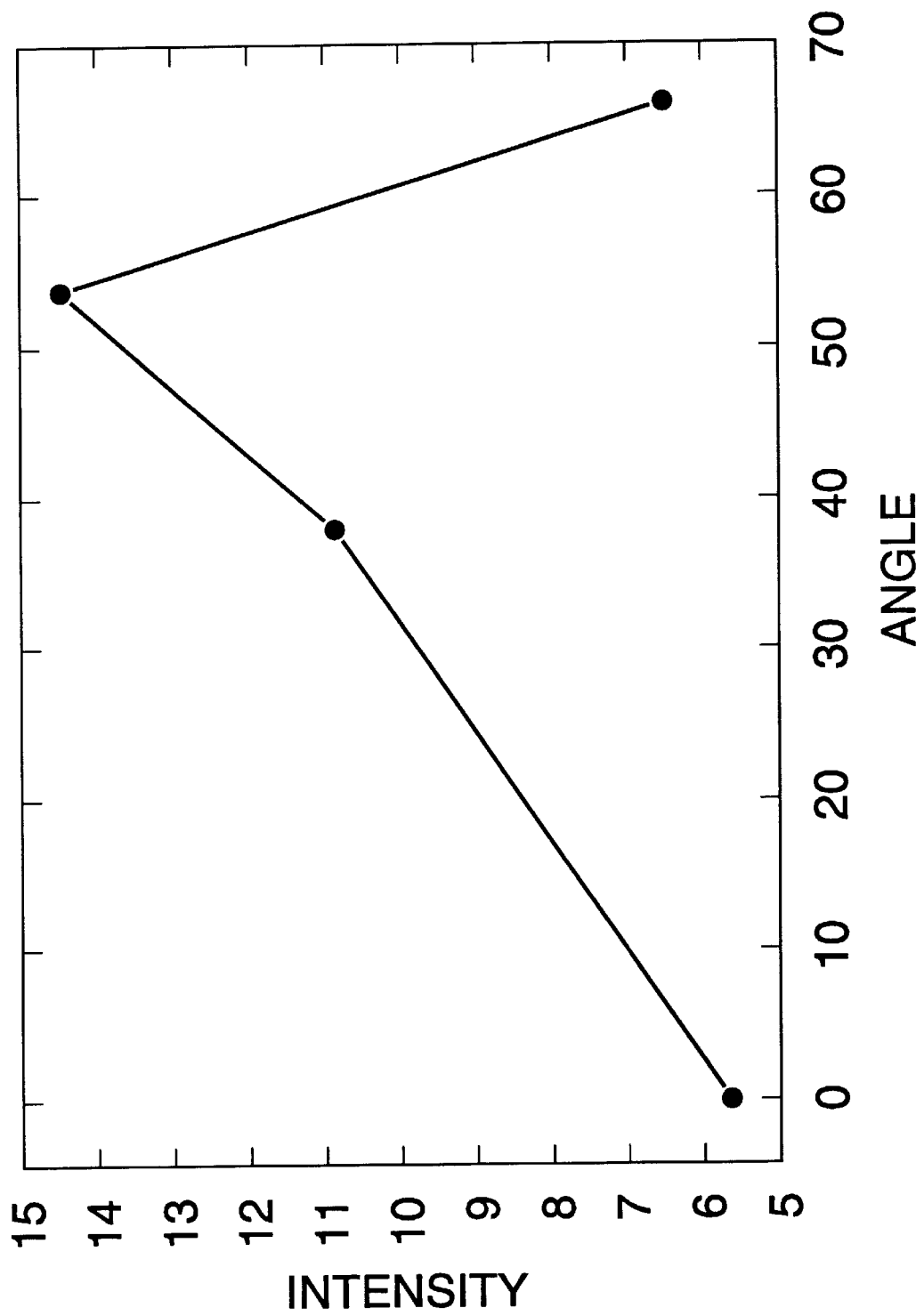
FIG. 5 shows a plot of absolute Raman intensity versus angle.

FIG. 4 shows the Raman spectra of carbon tetrachloride measured with three different angles of the slanted-tip fiberoptic probe compared with that measured with the flat-tip fiberoptic probe by Dai et al. This experiment was performed with the same fiberoptic probe, with the initial measurement utilizing the flat-tip probe with a 0° angle, then the next three measurements utilizing the fiberoptic probe with probe tip angles of 39°, 54° and 66°. The angle of the probe tip was changed by grinding and polishing a new angle between each spectral measurement. The same fiberoptic probe was used in each measurement so both the collection and exciting optical fibers remained fixed during the course of the experiment, thereby eliminating the possibility of any differences due to coupling efficiencies. FIG. 5 shows the plot of absolute Raman intensity versus angle. From the plot, it is indicated that a slant angle of 54° may be optimum for this specific application. The Raman spectrum of FIG. 4 also reflects this conclusion. The plot also shows that a slanted-tip fiberoptic probe 1 of FIG. 1 yields a more intense Raman spectra than a flat-tip fiberoptic probe with a 0° angle, thus the slanted-tip fiberoptic probe has a greater collection efficiency.

The optimum angle for the slant is related to the effective index of refraction of the sample medium. Essentially the effective refractive index controls the diameter of the viewing cones 27 and 25 of FIG. 2 of the exciting and collection optical fibers, and therefore influences the overlap 14. Any angle greater than 0°, particularly between 10° and 85°, is going to show improvement in scattered light collection over that of a flat-tip fiberoptic probe. It is probable that an angle of about 50° will be optimum for most applications.

Figure 6:
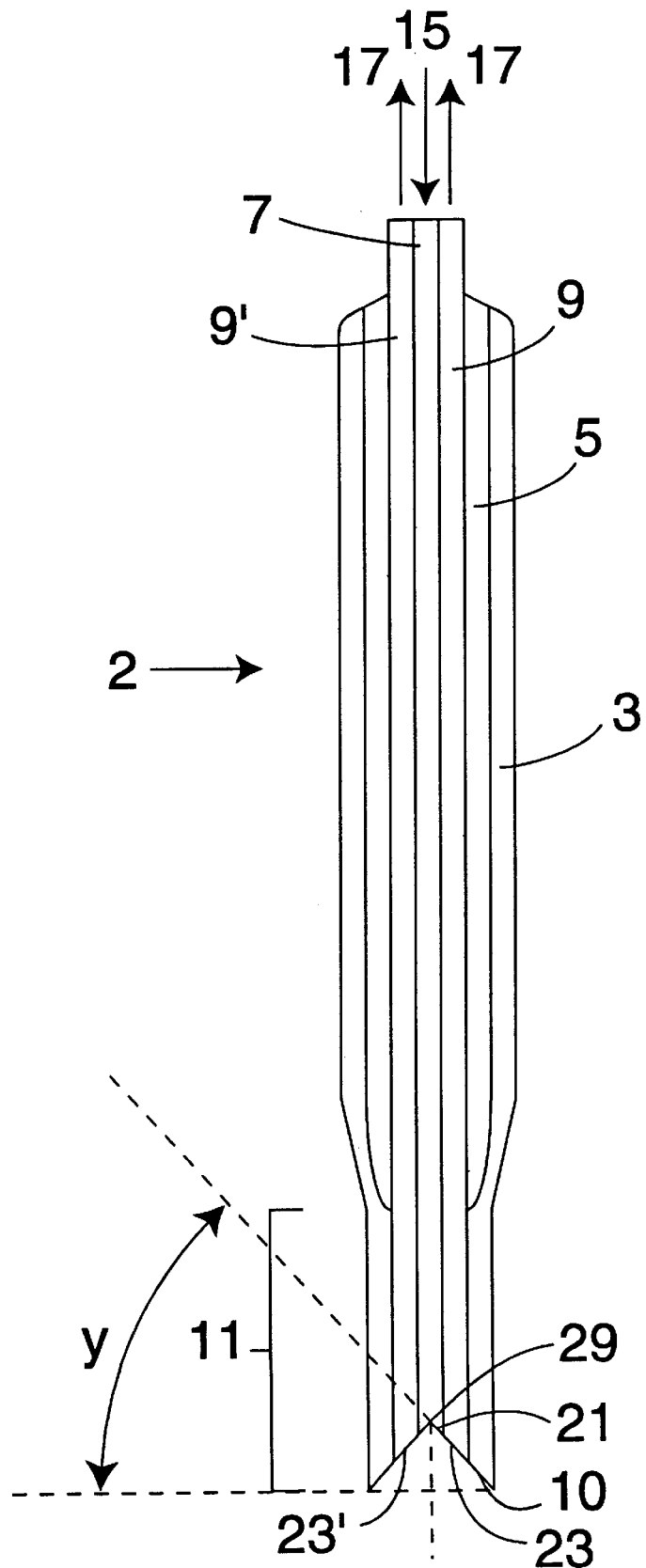
FIG. 6 illustrates, in accordance with another embodiment of the invention, a sectional view of a fused fiberoptic probe with the probe head having a conical indentation at its tip, co-axial with the longitudinal axis, forming having an inverted cone-shaped probe tip with the exciting optical fiber positioned at the center apex of the cone and at least two collection optical fibers juxtaposed with the exciting optical fiber.
Figure 7:
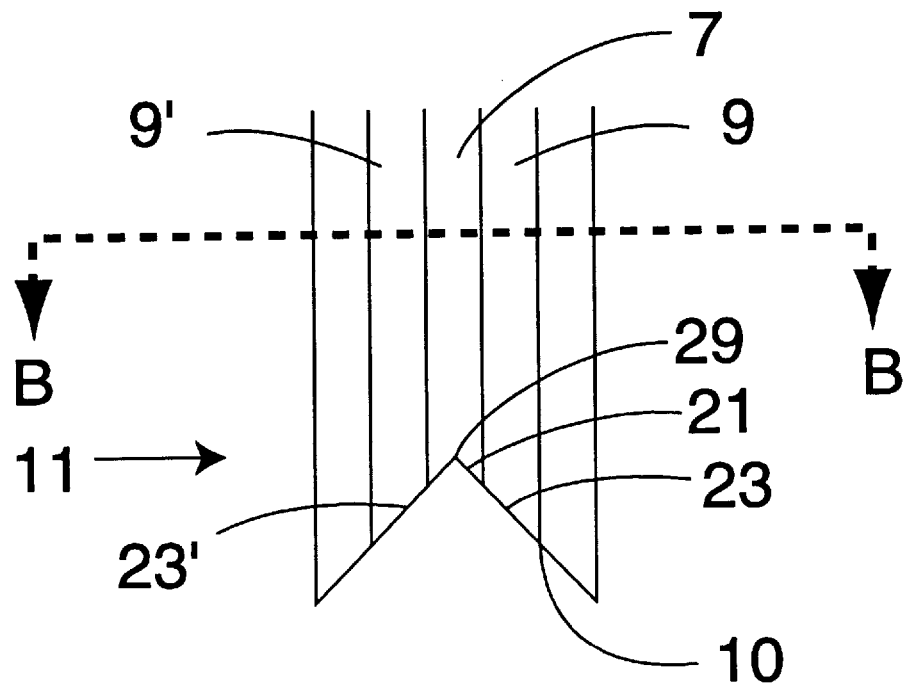
FIG. 7 shows the probe head of the inverted cone-shaped fiberoptic probe of FIG. 6 with a cross-sectional cut.
Figure 8:
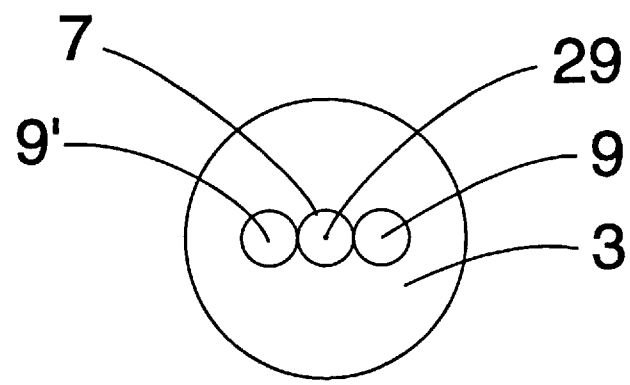
FIG. 8 shows the cross-sectional view from FIG. 7, illustrating the positions and closeness of the exciting optical fiber and the collection optical fibers to one another within the housing of the fiberoptic probe.
Figure 9:
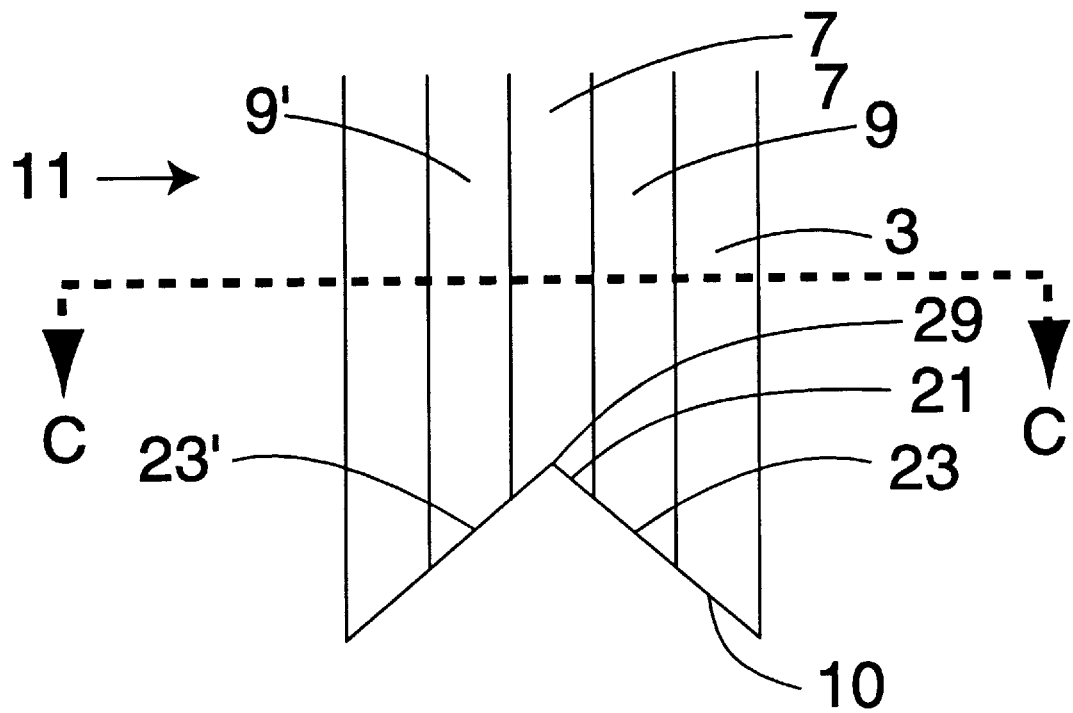
FIG. 9 shows the probe head of the preferred embodiment of the inverted cone-shaped fused fiberoptic probe having one exciting optical fiber positioned at the center apex of the cone and six collection optical fibers juxtaposed with the exciting optical fiber.
Figure 10:
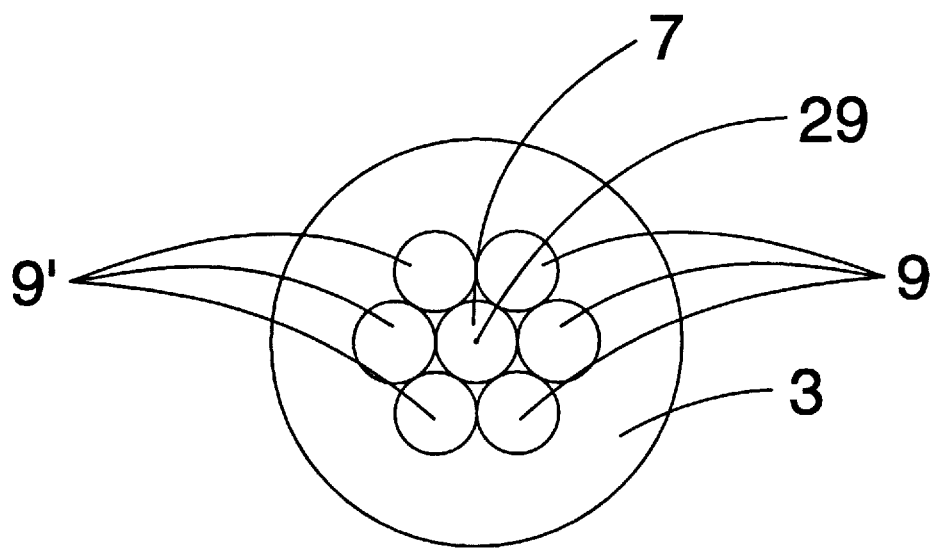
FIG. 10 shows the cross-sectional view from FIG. 9, illustrating the position and closeness of the exciting optical fiber and the six collection optical fibers to one another within the housing of the fiberoptic probe.

FIG. 6 shows another embodiment of a fiberoptic probe 2 wherein the probe tip 10 has the geometrical configuration of a concial indentation at its tip, co-axial with the longitudinal axis, forming an inverted cone, wherein the optical coupling of each collection optical fiber is optimized. This embodiment 2 of the fiberoptic probe comprises a probe head 11 having a probe tip with the shape of an inverted cone 10, an exciting optical fiber 7 and at least two collection optical fibers 9, 9'. The exciting optical fiber 7 is for transmitting exciting optical energy 15 from an energy source to the probe tip 10 in order to generate an optical signal 17 within a sample medium. The collection optical fibers 9, 9' are for transmitting the optical signal 17 from the probe tip. The figure shows the exciting optical fiber 7 having a terminus 21 at the center apex 29 of the cone, with the collection optical fibers 9 and 9' juxtaposed with the exciting optical fiber 7, surrounding the exciting optical fiber. The collection optical fibers have terminuses 23 and 23' juxtaposed with the exciting optical fiber terminus 21, therefore surrounding the center apex 29. The fusion of the housing 3 and the exciting and collection optical fibers are within the conical surface of the inverted cone and thus form the conical indentation of the probe head 11, as with the slanted tip fiberoptic probe of FIG. 1. The fusion step created the air pockets 5. The geometry of the inverted cone-shaped probe tip 10 is actually a multiple slanted-tip fiberoptic probe, a three-dimensional slanted-tip fiberoptic probe. The multiplicity is equal to the number of collection optical fibers 9, 9' that are juxtaposed with the exciting optical fiber 7 at the apex of the cone 29. Since each collection optical fiber 9, 9' is immediately adjacent and tangentially touching the exciting optical fiber, maximum collection efficiency of the collection optical fibers is realized. Again, this unique feature is possible because of the construction of the fused fiberoptic probe 2. FIG. 6 shows the probe head 11 having a longitudinal axis intersecting the apex of the inverted cone. A perpendicular axis is also shown intersecting the longitudinal axis at the probe head and probe tip. The terminuses of the exciting optical fiber and the collection optical fibers are angled toward the longitudinal axis at an angle between 10° and 85° with respect to the perpendicular axis. The angle y, representing the conical indentation of the inverted cone, as well as the angle of the terminuses of the optical fibers at the probe tip 10, depends upon the effective refractive index of the sample with an optimum angle between 10°0 and 85°. FIG. 7 shows a sectional view of the probe head 11 with a cross-cut B with the exciting optical fiber 7 having its terminus 21 at the center apex 29 of the inverted cone probe tip 10, collection optical fibers 9 and 9' being juxtaposed with the exciting optical fiber 7 with their terminuses 23 and 23' at the probe tip 10, fused within housing 3. FIG. 8 shows the cross-cut view from FIG. 7, illustrating the closeness and positions of the collection optical fibers 9 and 9' surrounding and juxtaposed with the exciting optical fiber 7 within the housing 3. The center apex 29 of the inverted cone can be seen in the center of the exciting optical fiber 7 since the exciting optical fiber 7 is positioned at the center apex 29. The preferred embodiment of the inverted cone-shaped fiberoptic probe 2 has six collection optical fibers surrounding and juxtaposed with the exciting optical fiber as shown in FIG. 9 and FIG. 10. FIG. 9 shows a sectional view of the probe head 11 with the exciting optical fiber 7 having its terminus 21 at the center apex 29 of the inverted cone probe tip 10, collection optical fibers 9 and 9' juxtaposed with the exciting optical fiber 7 with their terminuses 23 and 23' at the probe tip 10, fused within housing 3. FIG. 10 shows the cross-cut view from FIG. 9, illustrating the closeness and positions of the collection optical fibers 9 and 9' surrounding and juxtaposed with the exciting optical fiber 7 within the housing 3. The center apex 29 of the inverted cone can be seen in the center of the exciting optical fiber 7 since the exciting optical fiber 7 is positioned at the center apex 29.

The embodiment shown in FIG. 6 is very useful for reflectance spectroscopy since it results in more efficient collection of scattered light. The inverted cone-shaped probe tip 10 of the fiberoptic probe 2 can also act as a cuvette or a spectroscopy container when the probe is inverted, holding a very small volume of sample, either liquid or solid. For example, if the probe tip comprised one exciting optical fiber and six collection optical fibers of 100 μm in diameter, the seven optical fibers in this inverted conical tip (cone angle approximately 50°) would be covered by only 4 nl of liquid. Such an embodiment would be useful for microspectrophotometry, Raman, fluorescence or absorption. This probe tip would be useful for fluorescence studies of materials adsorbed on single resin beads of about 100 μm in diameter. The collection efficiency is very high with this embodiment. Solid, liquid or powder samples can be analyzed using this probe and method.

A third embodiment of Applicants' invention is useful for spectroelectrochemical analysis. This embodiment involves coating the exciting optical fiber with any metal, particularly gold, aluminum, platinum, tungsten, tantalum or alloys thereof. This embodiment can be applied to the slanted-tip probe 1 of FIG. 1 or, more preferably, the inverted cone-shaped probe 2 as shown in FIG. 6. The collection optical fibers are all silica and the housing is made of glass, such as fused silica or pyrex. The glass prevents any melting of metal during the fusion process. By using a metal-coated silica optical fiber as the exciting optical fiber, a potential can be placed on the metal ring that is formed at the probe tip at the terminus of the exciting optical fiber, then the cone-shaped probe, when operated in the inverted mode, is useful for microspectroelectrochemistry. The metal-coated exciting optical fiber generates optically active species with this micro electrode, then the information (fluroescence, Raman, etc.) is collected by the collection optical fibers on the small volume (possibly 3 nl or less) of sample contained in the cone of the probe tip.

Another embodiment of the cone-shaped fiberoptic probe 2 of FIG. 6 involves inverting the conical probe and adding dropwise or pouring sol gel into the cone in an amount sufficient to fill the area within the cone and allowing the sol gel to harden by drying the probe vertically in the open air. The hardened sol gel acts as a lens having a convex, concave or flat shape, not illustrated. The sol gel may contain reagents, such as a bioanalytical coupling reagent like a fluorescent indicator or a pH indicator, entrapped within the sol gel. Reagents are entrapped in sol-gel using a method such as that described by Ovadia Lev et al in 1992 in *Fresenius Journal of Analytical Chemistry*, volume 343, pages 370–372. The sol gel-filled conical fiberoptic probe can be used as a probe having a lens that is flat, concave or convex in shape so that data from an optical signal can be collected from a distance.

Figure 11:
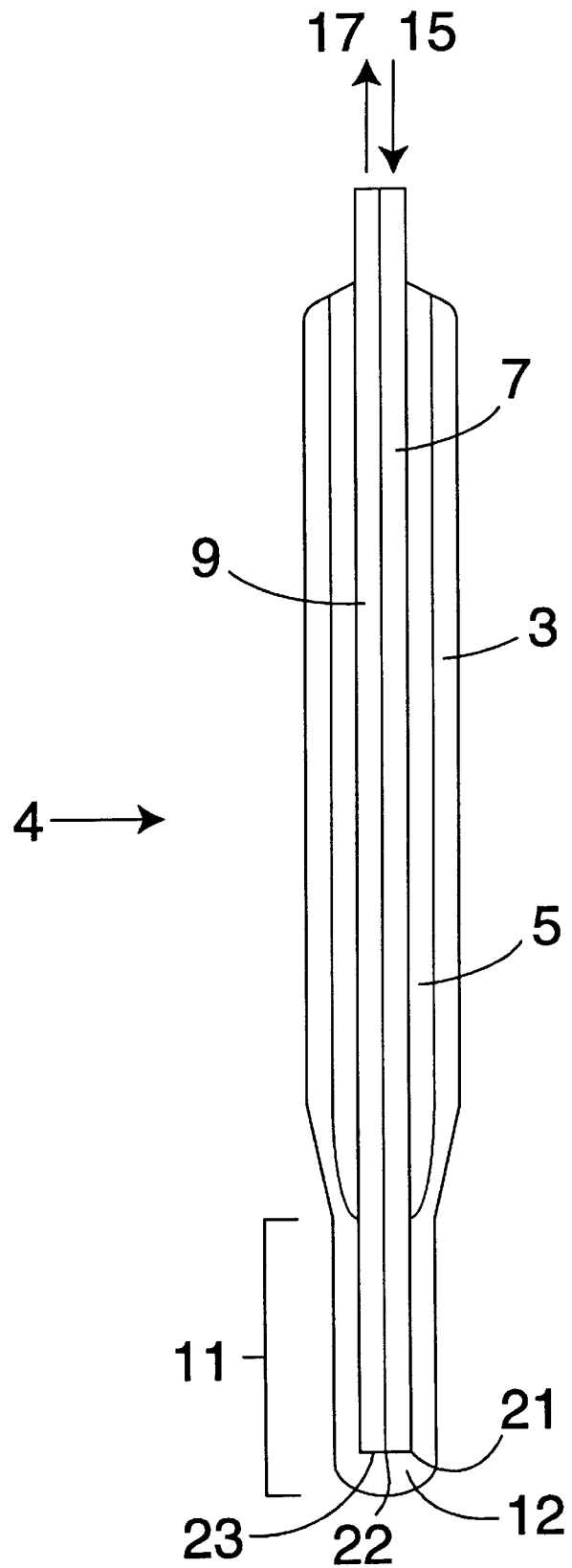
FIG. 11 shows a sectional view of a fused fiberoptic probe with the probe head having a probe tip with a lens disposed on the probe tip, in accordance with another embodiment of the invention.

FIG. 11 shows yet another embodiment of the fiberoptic probe 4. This particular embodiment comprises the same probe body style as in FIG. 1, except that the probe head 11 has a convex lens 12 disposed on the probe tip 22 wherein the housing extends beyond the terminuses 21 and 23 of the optical fibers 7 and 9, (which make up the probe tip), to form the lens. The lens can also be disposed on the probe tip 22 by using a sol-gel technique. The lens head fiberoptic probe 4 comprises a probe head having a convex lens 12 disposed on the probe tip 22, an exciting optical fiber 7 and at least one collection optical fiber 9 fused within a housing 3 at the probe head, thereby forming the probe head. The exciting optical fiber 7 has a terminus 21 at the probe tip 22, thereby forming the probe tip. The exciting optical fiber is for transmitting exciting optical energy 15 to the probe tip in order to generate an optical signal 17 within the sample medium. The collection optical fiber 9 has a terminus 23 at the probe tip 22 for transmitting the optical signal 17 from the probe tip 22 to a signal analyzer. The probe head 11 is the region of the probe where the fusion of the optical fibers 7, 9 and the housing 3 occur, creating an air pocket 5 between the housing and optical fibers on the upper body of the probe. The housing 3 and the optical fibers 7, 9 are silica. The lens 12 can be made by two different techniques. One technique involves heating silica at a higher temperature than the temperature required to fuse the optical fibers with the housing, thus sealing the housing. Then the housing is cut beyond the terminuses of the optical fibers and a lens is ground using standard optical fabrication techniques as described by E. B. Shand in the *Glass Engineering Handbook*, chapter 9 (1958). The second technique is for the lens to be made by adding a drop of sol gel to the probe tip 22 or dip-coating the probe tip in the sol-gel solution. A fiberoptic probe with the probe tip 22 covered with a sol-gel lens was fabricated by the applicants. Sodium silicate solution was used as a sol-gel starting material. The probe tip was dip-coated with the solution and dried vertically in the open air. Gravity and surface tension deformed the shape of the sol-gel naturally into a semi-sphere.

The fabrication of the fiberoptic probe 1 of FIG. 1 involved flame fusing at least two 600 μm diameter optical fibers (C-Technology, Short Hills, N.J.) into a housing, preferrably an all-silica tube, with the tube being under a partial vacuum (less than 0.5 atmosphere). Optical fibers with various other diameters can also be used, such as 200 $\mu$m and 400 $\mu$m. The optical fibers can be of varying lengths as well, depending upon the intended application of the fiberoptic probe. The optical fibers were fused with the all-silica housing tube. The housing tube for the microspectroelectrochemistry embodiment is glass, such as pyrex or fused silica. The optical fibers have an outer coating of polyimide, but the polyimide coating around the fusion region of each fiber was removed by the flame of a torch before the fibers were fused. The region of the fiberoptic probe where fusion took place, probe head 11, can be seen in FIG. 1, FIG. 6 and FIG. 7. The application of the reduced pressure, mentioned above, during fusion was crucial while pulling the tube around the fibers, in order to make a vacuum tight seal at the probe tip and to prevent bubbling during the closure. The fusion process involved heating the region of the fiberoptic probe 11 to be fused to a temperature sufficient to effect total fusion wherein the optical fibers were fused with the housing. The fusion method used was very similar to those methods used in the fabrication of microelectrodes. An example of this fusion method can be found in *Analytical Chemistry* volume 63, (1991), page 78 by C. Lee, C. J. Miller and A. J. Bard. Once fused, the sealed end of the probe tip was cut. When the above fabrication was complete, the probe head having a probe tip was essentially a silica rod in which the probe tip was then shaped into the desired geometrical configuration mentioned above, using standard optical fabrication techniques as described in chapter 9 of the *Glass Engineering Handbook*, McGraw-Hill 1958 by E. B. Shand. Upon construction of the slanted-tip fiberoptic probe, microscopic examination of the probe tip during illumination of the optical fibers revealed no light being emitted from the surrounding silica tube. This implied that the fiber cladding materials were preserved during the fusion process and the individual optical fibers remained intact.

The slanted-tip embodiment and other embodiments thereof present a significant improvement in design as it is made from fused silica with no cement involved. It is essentially a silica rod that operates over the temperature range in which silica remains solid (absolute 0 to 1800 K). Silica has a very low coefficient of thermal expansion. It has good stability to radiation effects as well as the thermal, optical, and corrosion resistance attributes of pure silica. Therefore, the probe can tolerate these temperature extremes and high radiation fields without failure. The ability to obtain varied kinds of spectral information, not just Raman or absorption, over such a wide range of temperatures and conditions is the unique feature of Applicants' fiberoptic probe. At 77 K, or below, since the probe can be in intimate contact with the sample, no bubbling of liquid nitrogen or helium is present to interfere with data collection. In corrosive molten chloride salts, the collection of Raman spectra is not affected even when the probe and silica sheath are etched. The probe works as a general purpose fiberoptic probe because it can scatter exciting light and can collect nearby scattered light.

Figure 12:
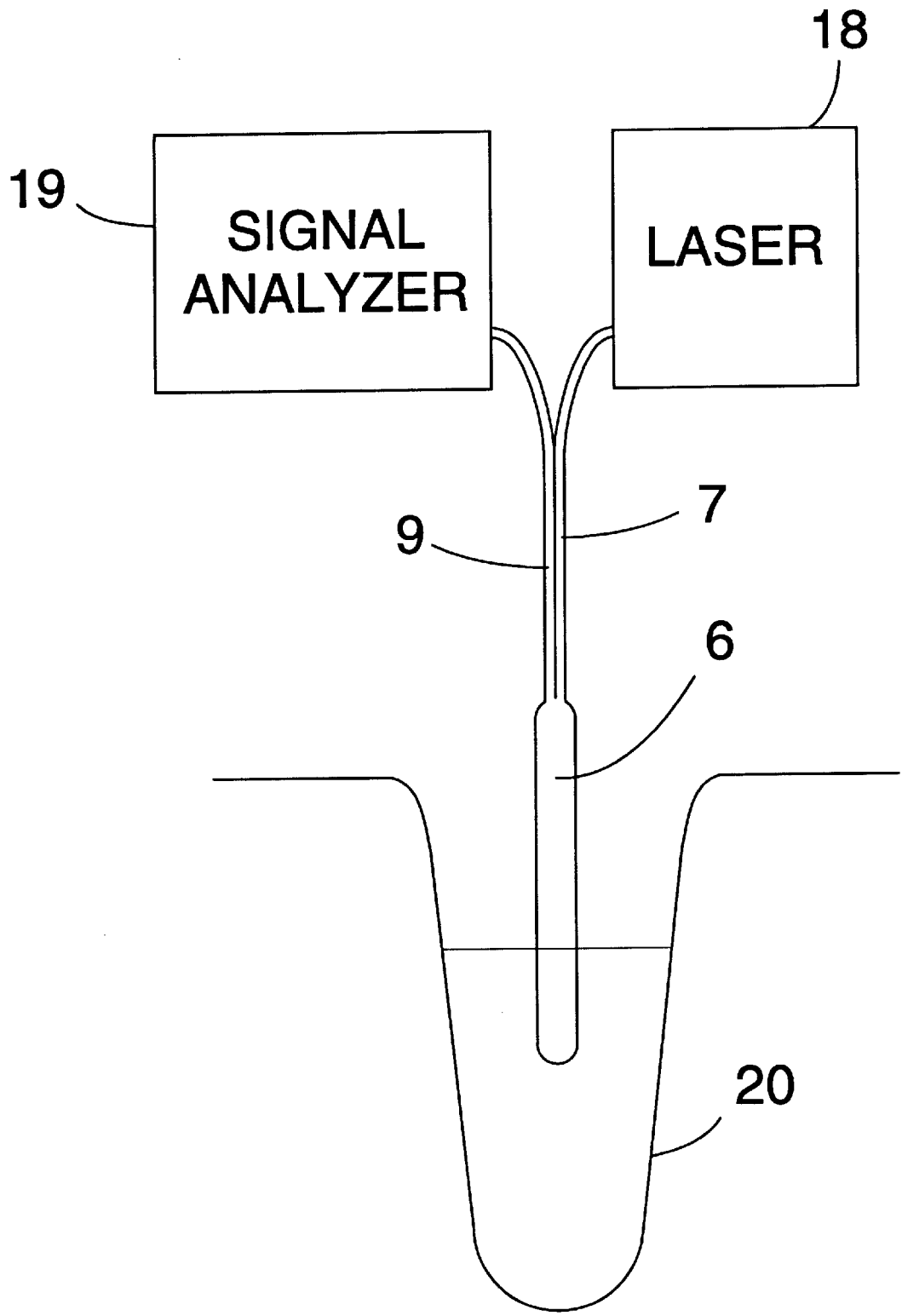
FIG. 12 shows a system for conducting spectral measurements utilizing a fused fiberoptic probe, in accordance with the invention.

FIG. 12 shows a system for conducting spectral measurements utilizing a fiberoptic probe 6 wherein the exciting optical fiber 7 extends beyond the fiberoptic probe body to an optical energy source 18, such as an argon-ion laser. The collection optical fiber 9 extends beyond the fiberoptic probe body to a signal analyzer 19, such as a Ramanor HG.2S spectrophotometer by Jobin-Yvon Instruments SA. This particular instrument uses a double monochromator equipped with curved holographic gratings. A S-20 type cooled photomultiplier tube can be used with pulse counting electronics and a Nicolet 1170 signal averager to collect data. The system in use directs the optical energy from the optical energy source 18 onto the exciting optical fiber 7. The exciting optical fiber 7 then transmits the optical energy to the probe tip and then from the probe tip into the sample medium 20 to generate an optical signal within the sample. At least one collection optical fiber collects the optical signal through the probe tip and transmits the optical signal up the collection optical fiber to the signal analyzer 19. Spectra can then be processed with a personal computer and commercially available data acquisition software. All of these are described in the Dai et al publication. FIG. 12 shows the fiberoptic probe 6 immersed in a sample 20.

While there has been shown and described what are at present considered the preferred embodiments of the invention, it will be obvious to those skilled in the art that various changes and modifications can be made therein, without departing from the scope of the invention defined by the appended claims.

What is claimed is:

1. A fused fiberoptic probe for conducting spectral measurements comprising:
  a. an exciting optical fiber having a terminus;
  b. at least two collection optical fibers, each having a terminus;
  c. an immersible probe head enclosing the terminuses of and being fused to said exciting optical fiber and said collection optical fibers, said immersible probe head having a longitudinal axis, said probe head further having a probe-tip having a conical indentation at its tip, said conical indentation being co-axial with said longitudinal axis, said conical indentation defining a conical surface of an inverted cone-shaped probe tip wherein said terminuses of said exciting optical fiber and said collection optical fibers are within the conical surface of the inverted cone of the conical indentation and thus are angled toward said longitudinal axis at an angle between 10° and 85°, said angle being dependent upon the effective refractive index of a sample medium, said inverted cone-shaped probe tip having a center apex, said center apex being intersected by said longitudinal axis;
  d. said exciting optical fiber having said terminus at said center apex of said inverted cone-shaped probe tip, said exciting optical fiber for transmitting exciting optical energy to said probe tip in order to generate an optical signal within said sample medium; and
  said collection optical fibers being juxtaposed with said exciting optical fiber, said collection optical fibers for transmitting said optical signal from said probe tip.

2. The fiberoptic probe in accordance with claim 1 wherein said optical signal comprises a Raman signal.

3. The fiberoptic probe in accordance with claim 1 wherein said exciting optical fiber has a metal coating.

4. The fiberoptic probe in accordance with claim 3 wherein said optical fibers are fused within a housing of glass.

5. A method for conducting spectral measurements comprising the steps of:
  a. providing a fused fiberoptic probe comprising an exciting optical fiber having a terminus, at least two collection optical fibers, each having a terminus, an immersible probe head enclosing the terminuses of and being fused to said exciting optical fiber and said collection optical fibers, said imnnersible probe head having a longitudinal axis, said probe head further having a probe-tip having a conical indentation at its tip, said conical indentation being co-axial with said longitudinal axis, said conical indentation defining a conical surface of an inverted cone-shaped probe tip wherein said terminuses of said exciting optical fiber and said collection optical fibers are within the conical surface of the inverted cone of the conical indentation and thus are angled toward said longitudinal axis at an angle between 10° and 85°, said angle being dependent upon the effective refractive index of a sample medium, said inverted cone-shaped probe tip having a center apex, said center apex being intersected by said longitudinal axis, said exciting optical fiber having said terminus at said center apex of said inverted cone-shaped probe tip, said exciting optical fiber for transmitting exciting optical energy to said probe tip in order to generate an optical signal within said sample medium, said collection optical fibers being juxtaposed with said exciting optical fiber said collection optical fibers for transmitting said optical signal from said probe tip;

b. immersing said probe head into said sample medium;

c. transmitting exciting optical energy into said exciting optical fiber wherein said exciting optical energy is transmitted to said probe tip for generating an optical signal within said sample medium; and d. transmitting said optical signal from said probe tip through said collection optical fibers to a signal analyzer.

6. The method for conducting spectral measurements in accordance with claim 5 wherein said optical signal comprises a Raman signal.

7. The method for conducting spectral measurements in accordance with claim 5 wherein said exciting optical fiber has a metal coating.

8. The method for conducting spectral measurements in accordance with claim 7 wherein said optical fibers are fused within a housing of glass.

9. A method for conducting spectral measurements comprising the steps of:

a. providing a fused fiberoptic probe comprising an exciting optical fiber having a terminus, at least two collection optical fibers each having a terminus, an immersible probe head enclosing the terminuses of and being fused to said exciting optical fiber and said collection optical fibers, said immersible probe head having a longitudinal axis, said probe head further having a probe-tip having a conical indentation at its tip, said conical indentation being co-axial with said longitudinal axis, said conical indentation defining a conical surface of an inverted cone-shaped probe tip wherein said terminuses of said exciting optical fiber and said collection optical fibers are within the conical surface of the inverted cone of the conical indentation and thus are angled toward said longitudinal axis at an angle between 10° and 85°, said angle being dependent upon the effective refractive index of a sample medium, said inverted cone-shaped probe tip having a center apex, said center apex being intersected by said longitudinal axis, said exciting optical fiber having said terminus at said center apex of said inverted cone-shaped probe tip, said exciting optical fiber for transmitting exciting optical energy to said probe tip in order to generate an optical signal within said sample medium, said collection optical fibers being juxtaposed with said exciting optical fiber, said collection optical fibers for transmitting said optical signal from said probe tip;

b. disposing said fiberoptic probe wherein said conical indentation serves as a spectroscopic container;

c. placing a sample within said conical indentation;

d. transmitting exciting optical energy into said exciting optical fiber wherein said exciting optical energy is transmitted to said probe tip for generating an optical signal within said sample medium; and e. transmitting said optical signal from said probe tip through said collection optical fibers to a signal analyzer.

10. The method for conducting spectral measurements in accordance with claim 9 wherein said optical signal comprises a Raman signal.

11. The method for conducting spectral measurements in accordance with claim 9 wherein said exciting optical fiber has a metal coating.

12. The method for conducting spectral measurements in accordance with claim 11 wherein said optical fibers are fused within a housing of glass.

\* \* \* \* \*